United States Patent [19]

Connor et al.

[11] 4,104,274

[45] Aug. 1, 1978

[54] 1-SUBSTITUTED-2-(2-PYRIDINYL)ETHANONE N-OXIDES

[75] Inventors: David T. Connor, Parsippany; Patricia A. Young, Madison; Maximilian von Strandtmann, Rockaway Township, Morris County, all of N.J.

[73] Assignee: Warner-Lambert Company, MorrisPlains, N.J.

[21] Appl. No.: 825,011

[22] Filed: Aug. 16, 1977

Related U.S. Application Data

[62] Division of Ser. No. 611,282, Sep. 8, 1975, Pat. No. 4,056,619.

[51] Int. Cl.² .......................................... C07D 213/89
[52] U.S. Cl. ........................................... 260/295 AM
[58] Field of Search .................................. 260/295 AM

[56] References Cited

U.S. PATENT DOCUMENTS 4,056,619  11/1977  Connor et al. ..................... 424/263

OTHER PUBLICATIONS

Chemical Abstracts vol. 85, abst. No. 177349b (1976) (abst. of Preuss et al).

*Primary Examiner*—John D. Randolph
*Attorney, Agent, or Firm*—Albert H. Graddis; Frank S. Chow; Anne M. Kelly

[57] ABSTRACT

1-Substituted-2-(2-pyridinyl)ethanone N-oxides having the formula I or II:

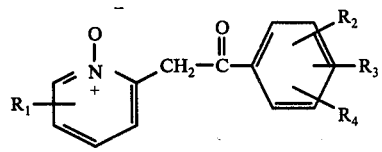

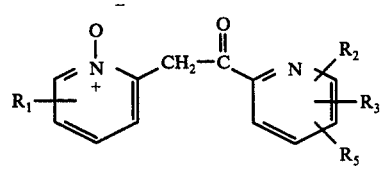

wherein $R_1$ is hydrogen or lower alkyl; $R_2$ and $R_3$ are each hydrogen, halogen, hydroxy, lower alkyl, lower alkoxy, or benzyloxy; $R_4$ is halogen, hydroxy, lower alkyl, lower alkoxy, benzyloxy, ortho-amino, ortho-lower alkylamino, ortho-alkanoylamino or ortho benzoylamino; and $R_5$ is hydrogen, halogen, hydroxy, lower alkyl, lower alkoxy or benzyloxy; the pharmaceutically acceptable acid addition salts thereof, and a process for the preparation thereof, are described. The compounds of this invention are useful for the treatment of allergic conditions and for the treatment of hyperacidity.

1 Claim, No Drawings

1-SUBSTITUTED-2-(2-PYRIDINYL)ETHANONE N-OXIDES

This is a division, of application Ser. No. 611,282 filed Sept. 8, 1975, now U.S. Pat. No. 4,056,619 granted Nov. 1, 1977.

DESCRIPTION OF THE PRIOR ART

Osborne et al., in J. Heterocyclic Chem. 1: 138-140 (1964), describe the preparation of 1-phenyl-2-(2-pyridinyl)ethanone N-oxide by the acylation of 2-picoline N-oxide, using sodium amide in liquid ammonia as the condensing agent. No pharmacological activity is reported for this or related compounds described by Osborne et al.

DESCRIPTION OF THE PARTICULAR EMBODIMENTS

This invention relates to 1-substituted-2-(2-pyridinyl) ethanone N-oxides having the formula I or II:

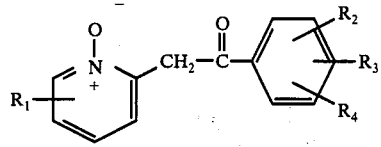

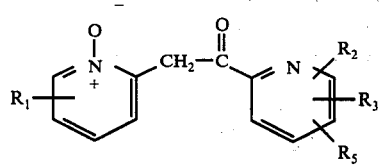

wherein $R_1$ is hydrogen or lower alkyl; $R_2$ and $R_3$ are each hydrogen, halogen, hydroxy, lower alkyl, lower alkoxy, or benzyloxy; $R_4$ is halogen, hydroxy, lower alkyl, lower alkoxy, benzyloxy, ortho-amino, ortho-lower alkyl-amino, ortho-alkanoylamino or benzoylamino; and $R_5$ is hydrogen, halogen, hydroxy, lower alkyl, lower alkoxy or benzyloxy; and the pharmaceutically acceptable acid addition salts thereof. Compounds of the formula I or II wherein $R_1$ is hydrogen; $R_2$ and $R_3$ are each hydrogen, halogen, methyl or methoxy; $R_4$ is halogen, hydroxy, methyl, methoxy, benzyloxy, ortho-amino, ortho-monomethylamino, or ortho-benzoylamine; and $R_5$ is hydrogen, halogen, hydroxy, methyl, methoxy or benzyloxy, as well as their pharmaceutically acceptable acid addition salts, are particularly preferred.

Many of the compounds of this invention may be prepared by reacting the correspondingly substituted benzoic acid ester with a substituted 2-picoline N-oxide in liquid ammonia in the presence of alkali metal amide condensing agent such as sodium, potassium or lithium amide, with sodium amide being preferred. This procedure is described generally by Osborne et al. in the above-mentioned J. Heterocyclic Chem. 1: 138-140 (1964). Compounds of the invention having the formula I (above) where $R_1$ is hydrogen or lower alkyl, $R_2$, $R_3$ and $R_4$ are limited to hydrogen, halogen, lower alkyl, lower alkoxy or benzyloxy may be prepared in this manner.

However, compounds of the invention having the formula III:

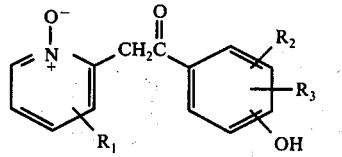

wherein $R_1$ is hydrogen or lower alkyl; and $R_2$ and $R_3$ are each hydrogen, halogen, hydroxy, lower alkyl, or lower alkoxy cannot be obtained directly from the correspondingly substituted benzoic acid ester. Thus, in order to prepare compounds having the formula III above, a substituted benzoic acid ester of the formula IV:

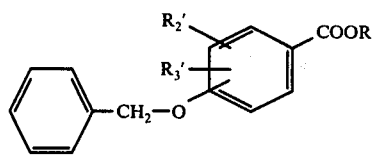

wherein R is lower alkyl and $R_2'$ and $R_3'$ are each hydrogen, halogen, lower alkyl, lower alkoxy or benzyloxy, is reacted with a substituted 2-picoline N-oxide of the formula V:

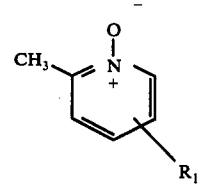

wherein $R_1$ is hydrogen or lower alkyl. The reaction is conducted in liquid ammonia, using an alkali metal condensing agent such as sodium, potassium or lithium amide. The sodium amide is preferred. This reaction produces an intermediate product of the formula VI:

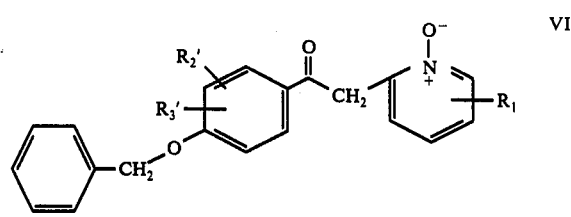

wherein $R_1$ is hydrogen or lower alkyl; and $R_2'$ and $R_3'$ are each hydrogen, halogen, lower alkyl, lower alkoxy or benzyloxy.

Intermediate VI is then subjected to catalytic reduction, using conventional methods. Typically, the reduction is conducted using gaseous hydrogen and a palladium-on-carbon catalyst. Ethyl acetate, acetic acid, or ethanol are suitable as solvents. The reaction proceeds most efficiently in the acetic acid solvent and it is therefore preferred. Thus, reduction of one or more benzyloxy substituents on intermediate compound VI provides the corresponding hydroxy-substituted compounds of the invention having formula III, above.

Similarly, compounds of the invention having the formula VII:

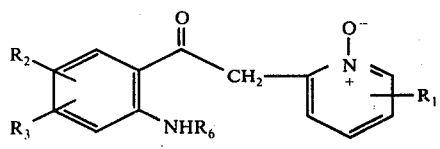

wherein $R_1$ is hydrogen or lower alkyl; $R_2$ and $R_3$ are each hydrogen, halogen, hydroxy, lower alkyl, lower alkoxy or benzyloxy; and $R_6$ is hydrogen or lower alkyl, cannot be obtained directly from the correspondingly substituted benzoic acid ester. In order to prepare compounds having the formula VII above, an N-substituted isatoic anhydride having the formula VIII:

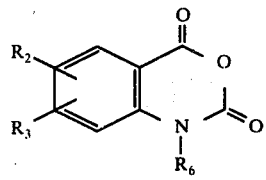

wherein $R_2$, $R_3$ and $R_6$ are as defined above, in VII, is reacted with a substituted 2-picoline N-oxide of the formula V:

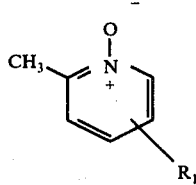

wherein $R_1$ is as defined above in VII. This reaction is conducted in liquid ammonia in the presence of an alkali metal amide condensing agent such as sodium, potassium or lithium amide (sodium amide preferred) to obtain the desired compounds of the invention having the formula VII, above.

Compounds of the invention having formula IX:

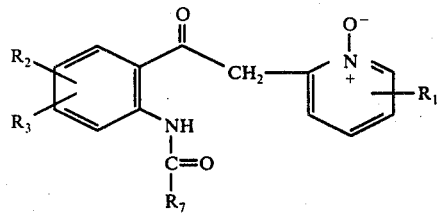

wherein $R_1$ is hydrogen or lower alkyl; $R_2$ and $R_3$ are each hydrogen, halogen, hydroxy, lower alkyl, lower alkoxy or benzyloxy; and $R_7$ is lower alkyl or phenyl; are prepared by reacting a substituted benzoxazine having the formula X:

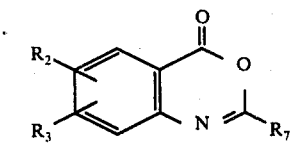

wherein $R_2$, $R_3$ and $R_7$ are as defined above in IX, with a substituted 2-picoline N-oxide of the formula V:

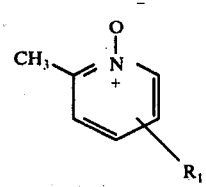

wherein $R_1$ is as defined above in IX in liquid ammonia in the presence of an alkali metal amide condensing agent such as sodium, potassium or lithium amide (sodium amide preferred).

In order to prepare those compound of the invention having formula XI:

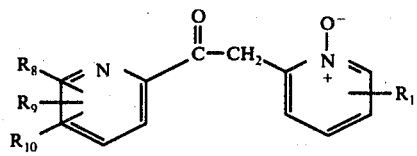

wherein $R_1$ is hydrogen or lower alkyl; $R_8$ and $R_9$ are each hydrogen, halogen, lower alkyl, lower alkoxy or benzyloxy; and $R_5$ is hydrogen, halogen, lower alkyl, lower alkoxy or benzyloxy; it is necessary to react a substituted-pyridine carboxylic acid ester of the formula XII:

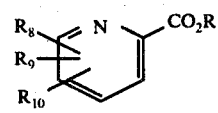

wherein R is a lower alkyl and $R_8$, $R_9$ and $R_{10}$ are as defined above in XI, with a substituted 2-picoline N-oxide of the formula V:

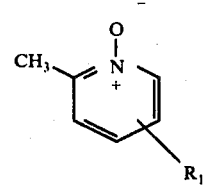

wherein $R_1$ is as defined above in XI. The reaction is conducted in liquid ammonia, using an alkali metal amide condensing agent such as sodium, potassium or lithium amide, (sodium amide preferred) to obtain an intermediate compound having the formula XIII:

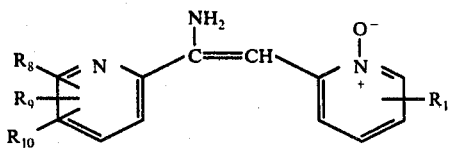

wherein $R_1$, $R_8$, $R_9$ and $R_{10}$ are as defined above in XI, which is subjected to hydrolysis to obtain the desired compound XI. The hydrolysis is conducted by heating compound XIII in boiling water.

Compounds of the invention having the formula XIV:

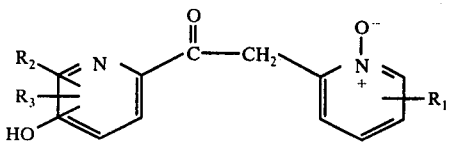

wherein $R_1$ is hydrogen or lower alkyl; and $R_2$ and $R_3$ are each hydrogen, halogen, hydroxy, lower alkyl or lower alkoxy; are prepared by reacting a substituted pyridinecarboxylic acid ester of the formula XV:

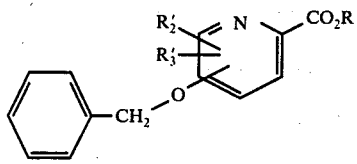

wherein R is lower alkyl; and $R_2'$ and $R_3'$ are each hydrogen, halogen, lower alkyl, lower alkoxy or benzyloxy; with a substituted 2-picoline N-oxide of the formula V:

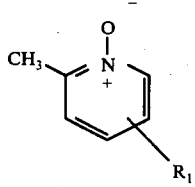

wherein $R_1$ is hydrogen or lower alkyl, in liquid ammonia in the presence of an alkali metal amide such as sodium, potassium or lithium amide (sodium amide preferred) to obtain an intermediate compound which is subjected to catalytic reduction to convert benzyloxy substituents to hydroxy groups. Typically, the reduction is conducted using gaseous hydrogen, a palladium-on-carbon catalyst, and an acetic acid catalyst.

The starting materials used to prepare the compounds of the invention in the above-described reactions are readily available or easily prepared by known methods. Representative starting materials include 3-methyl-pyridine-2-carboxylate; 3,4-dimethyl-pyridine-2-carboxylate; 4-methoxypyridine-2-carboxylate; 3,4-dimethoxypyridine-2-carboxylate; 3-bromo-pyridine-2-carboxylate; 4,6-dichloropyridine-2-carboxylate; and 4-benzyloxypyridine-2-carboxylate.

Pharmaceutically acceptable acid addition salts of the compounds of this invention are prepared according to conventional procedures by treating the free base form of the compounds of the invention in an alcoholic solution with the desired acid.

In the above formulas for the compounds of this invention, the R group definitions may be more fully described as follows: the term "lower alkyl" is meant to include lower aliphatic hydrocarbons having 1 to 7, preferably 1 to 4 carbon atoms in the alkyl chain, such as methyl, ethyl, propyl, isopropyl, butyl or isobutyl. This definition for lower alkyl also applies to the alkyl portions of "alkoxy" and "alkanoyl". The term "halogen" is meant to include bromine, chlorine, iodine and fluorine.

The compounds of this invention are active in the prevention of allergic conditions (typically, asthmatic reactions) in mammals such as rats and guinea pigs as evidenced by positive results in the passive cutaneous anaphylaxis screen (PCA test). The PCA screen is a modification of the procedures described by I. Mota, Life Sciences, Vol. 4, No. 7: 465–474 (1963) and Z. Ovary and O. Bier, Proc. Soc. Exptl. Biol. Med., 81: 584–586 (1952) and provides a measure of the effectiveness of test compounds in inhibiting the release or action of toxic products arising from the combination of reaginic antibodies with specific antigens. These toxic products are causative factors in such disorders as bronchial allergic asthma (extrinsic reagins), exercise asthma, cold asthma, hay fever, perennial allergic rhinitis, food allergies, serum or drug allergies, insect sting allergies, angioneurotic edema, atopic dermatitis, including infantile eczema, urticaria, dermographism, dermatoconjunctivities, acute allergic conjunctivitis, chronic allergic conjunctivitis, and the like.

Inhibition of reaginic antigen/antibody reactions in experimental animals such as rats and guinea pigs is regarded as representative of inhibition of human reaginic antigen/antibody ractions which occur during allergic episodes.

In the PCA screen, rats are sensitized with 1 mg of ovalbumin (Pentex, Kankakee, Ill.) intramuscularly and with $10^{10}$ B. pertussis organisms (Parke-Davis and Co., Detroit, Michigan; Bio. 210) intraperitoneally. On the 14 th day the animals are bled and the serum prepared in the usual manner. The reaginic nature of antiovalbumin serum thus obtained is verified by the use of standard criteria.

Passive cutaneous anaphylaxis is induced as described by Ovary and Bier (1952) and by Mota (1963). Suitable antibody concentration in 0.1 ml to result in reactions between 7 and 19 mm in diameter (usually 1:5 to 1:40 dilutions) are injected intradermally on either side of the dorsal midline of rats. Forty-eight hours later, the animals are dosed with drug and injected in the tail vein with 1 ml of saline containing 0.25% Evans blue and 1 mg ovalbumin. Thirty minutes later animals are sacrificed with ether, the dorsal skin reflected, and the mean orthogonal diameter of the reaction site measured.

A linear relationship can be shown to exist between the relative antibody concentration and the diameter of the resultant reaction if the antibody concentration is adjusted to yield diameters between approximately 7 and 19 mm. For each experiment, a line is fitted by the least squares method for the relationship of the diameter to the relative antibody concentration. This line is extrapolated to zero antibody concentration to derive the base-line diameter. The percentage inhibition due to drug treatment is then calculated by the formula:

% inhibition = $\left[ 1 - \frac{\text{(diameter of experimental } - \text{ base value)}}{\text{(diameter of control } - \text{ base value)}} \right] \times 100$ The significance of the inhibition is measured by Student's t-test.

For administration, the compounds are suspended by trituration in 1% gum tragacanth and 0.15M saline so as to give 10 ml/kg body weight.

Thus, the compounds of this invention are active for the inhibition of reagin-mediated allergic disorders when administered to mammals in need thereof at dose levels of from about 25 to about 50 mg/kg of body weight, by the oral or parenteral route. This dosage may be varied depending upon the severity of the condition, the age, weight, sex and class of mammal being treated, as well as the route of administration. For example, 1-(5-bromo-2-methoxphenyl)-2-(2-pyridinyl)ethanone N-oxide (the compound of Example 7) shows a 31% inhibition of the allergic response at 25 mg/kg when tested in the passive cutaneous anaphyalaxis (PCA) screen.

In addition to the above pharmacological activity, the compounds also exhibit gastric anti-secretory activity when tested according to the procedure described by H. Shay et al., *Gastroenterology*, 5: 43 (1945): In this last-mentioned test, male Long Evans Hooded rats (150–200 gms.) are fasted for 24 hours prior to testing (water ad lib). Rats are randomly divided into groups of 5 rats each and housed individually. At the time of testing, each rat is slightly anesthetised with ether, its stomach exposed through a midline abdominal incision and the pylorus ligated with silk thread. The incision is sutured closed and covered with Flexible Collodion, U.S.P. to prevent ingestion of blood. Test compound or vehicle control is administered (a) intraduodenally prior to closing the incision; (b) intraperitioneally immediately after ligation or (c) orally as a one hour pretreatment. Four hours later, the rats are sacrificed by ether and their stomachs removed and opened.

Gastric contents are placed in centrifuge tubes and centrifuged to remove debree. The volume of gastric juice is measured (expressed in milliliters) and titratable acidity determined electrometrically to pH 7.4 (expressed as milliequivalents of acid per liter). Results are expressed as percent reduction of volume and/or titratable acidity from control group average. Reduced gastric acid secretion in experimental animals in the above-described test is considered to be representative of pharmacological utility in the treatment of hyperacidity in humans.

Thus, the compounds of the invention are active in the treatment of hyperacidic conditions when administered to mammals at a dose level of from about 5 to about 20 mg/kg of body weight by the oral or parenteral route. This dosage may be varied depending on the severity of the condition, the age, weight, sex and class of mammal being treated, as well as the route of administration. For example, when 1-phenyl-2-(2-pyridinyl)ethanone N-oxide (the compound of Example 2) is tested in the pyloras ligated rat in the above-described procedure at a dose of about 20 mg/kg, intraperitioneally, a reduction of 57% in the volume of gastric acid and a reduction of 27.3% in the ion acid was obtained, compared to controls. Similarly, in this same test, 1-(4-methylphenyl)-2-(2-pyridinyl)ethanone N-oxide (the compound of Example 20) caused a reduction of 67.1% in the volume of gastric acid and a reduction of 49.2% in the ion acid, compared to controls.

In use, the compounds of the invention may be combined with parenterally acceptable vehicles, such as gum tragacanth, in saline suspension, to provide dosage forms suitable for parenteral administration; or they may be combined with pharmaceutical diluents such as lactose, cornstarch, and the like and formulated into tablet or capsule dosage forms.

To further illustrate the practice of this invention, the following examples are included:

EXAMPLE 1

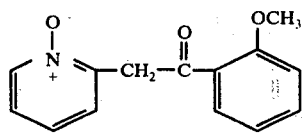

1-(2-Methoxyphenyl)-2-(2-pyridinyl)ethanone N-oxide

2-Picoline N-oxide (240g, 2.2m) is added to sodium amide (87g, 2.2m) in anhydrous liquid ammonia (2000ml). The resulting anion gives a deep red solution which is stirred for one hour and then ethyl 2-methoxybenzoate (200g, 1.1m) is added dropwise, giving a brown colored solution. This reaction mixture is stirred one hour, after which the reaction is quenched by the slow addition of solid ammonium chloride (120g, 2.2m). The ammonia is allowed to evaporate at room temperature. The contents of the flask are washed out with water and the insoluble solids are filtered, washed with several portions of fresh water, and sucked dry. This crude product is recrystallized from ethyl acetate to give light-beige crystals (134.8g, 50.5%), m.p. 116°–18° C.

Anal. Calcd. for $C_{14}H_{13}NO_3$: C, 69.12; H, 5.39; N, 5.76. Found: C, 68.84; H, 5.55; N, 6.00.

EXAMPLE 2

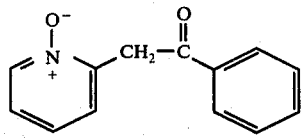

1-Phenyl-2-(2-pyridinyl)ethanone N-oxide*

*D. R. Osborne and R. Levin, J. Hetercyclic Chem. 1: 138-140 (1964).

Prepared by the general method described in Example 1 from methyl benzoate and 2-picoline N-oxide anion. Recrystallization from benzene/petroleum ether gives off-white crystals (9.3g, 43.5%), m.p. 158°–60° C.

Anal. Calcd. for $C_{13}H_{11}NO_2$: C, 73.22; H, 5.20; N, 6.57. Found: C, 72.94; H, 5.35; N, 6.48.

EXAMPLE 3

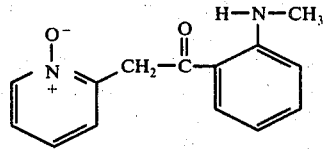

1-[2-(Methylamino)phenyl]-2-(2-pyridinyl)ethanone N-oxide

Prepared by the general method described in Example 1 from N-methyl isatoic anhydride and 2-picoline N-oxide anion. Recrystallization from ethyl acetate gives yellow-green crystals, (83.5g, 57%), m.p. 138-40° C.

Anal. Calcd. for $C_{14}H_{14}N_2O_2$: C, 69.49; H, 5.83; N, 11.56. Found: C, 69.43; H, 5.86; N, 11.54.

EXAMPLE 4

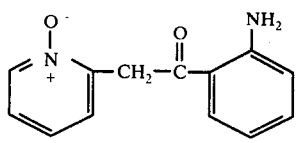

1-[2-aminophenyl]-2-(2-pyridinyl)ethanone N-oxide

Prepared by the general method described in Example 1 from isatoic anhydride and 2-picoline N-oxide annion. Recrystallization from absolute ethanol gives pale yellow crystals (52.8g, 58.5%), m.p. 172°–76° C.

Anal. Calcd. for $C_{13}H_{12}N_2O_2$: C, 68.41; H, 5.30; N, 12.27. Found: C, 68.49; H, 5.39; N, 12.21.

EXAMPLE 5

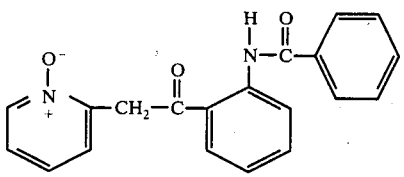

N-[2-(2-pyridinylacetyl)phenyl]benzamide N-oxide

Prepared by the general method described in Example 1 from Benzoylanthranil and 2-picoline N-oxide anion. Recrystallization from absolute ethanol gives pale yellow crystals (12.5g, 25.1%), m.p. 192°–94° C.

Anal. Calcd. for $C_{20}H_{16}N_2O_3$: C, 72.28; H, 4.85; N, 8.43. Found: C, 72.31; H, 4.99; N, 8.54.

EXAMPLE 6

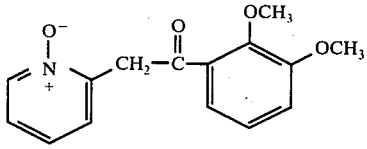

1-(2,3-Dimethoxyphenyl)-2-(2-pyridinyl)ethanone N-oxide

Prepared by the general method described in Example 1 from methyl 2,3-dimethoxy benzoate and 2-picoline N-oxide anion. Recrystallization from ethyl acetate gives light brown crystals (12.8g, 46%), m.p. 122°–24° C.

Anal. Calcd. for $C_{15}H_{15}NO_4$: C, 65.92; H, 5.53; N, 5.13. Found: C, 65.90; H, 5.57; N, 5.10.

EXAMPLE 7

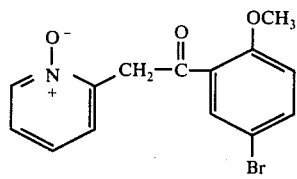

1-(5-Bromo-2-methoxyphenyl)-2-(2-pyridinyl)ethanone N-oxide

Prepared by the general method described in Example 1 from methyl 2-methyl-5-bromo-benzoate and 2-picoline N-oxide anion. Recrystallization from absolute ethanol gives light tan crystals (119g, 74.4%), m.p. 166°–68° C.

Anal. Calcd. for $C_{14}H_{12}BrNO_3$: C, 52.20; H, 3.76; N, 4.35; Br, 24.80. Found: C, 52.17; H, 3.79; N, 4.36; Br, 25.03.

EXAMPLE 8

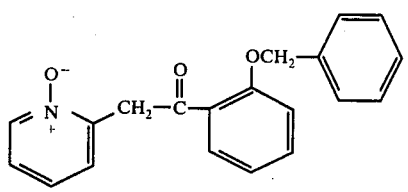

1-[2-(Phenylmethoxy)phenyl]-2-(2-pyridinyl)ethanone N-oxide

Prepared by the general method described in Example 1 from methyl 2-benzyloxy-benzoate and 2-picoline N-oxide anion. Recrystallization from ethyl acetate gives white crystals (52.3g, 79.5%), m.p. 138°–40° C.

Anal. Calcd. for $C_{20}H_{17}NO_3$: C, 75.22; H, 5.37; N, 4.39. Found: C, 75.37; H, 5.35; N, 4.32.

EXAMPLE 9

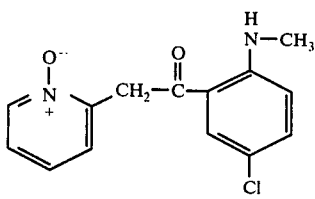

1-[5-Chloro-2-(methylamino)phenyl]-2-(2-pyridinyl)-ethanone N-oxide

Prepared by the general method described in Example 1 from 5-chloro N-methyl isatoic anhydride and 2-picoline N-oxide anion. Recrystallization from ehtyl acetate gives uyellow-green crystals (37.9g, 58%), m.p. 126°–28° C.

Anal. Calcd. for $C_{14}H_{13}ClN_2O_2$: C, 60.77; H, 4.74; N, 10.12; Cl, 12.81. Found: C, 60.51; H, 4.79; N, 10.23; Cl, 12.98.

EXAMPLE 10

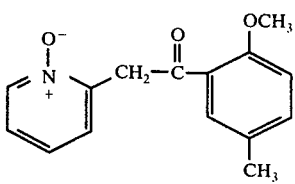

1-(2-Methoxy-5-methylphenyl)-2-(2-pyridinyl)ethanone N-oxide

Prepared by the general method described in Example 1 from methyl 2-methoxy-5-methylbenzoate and 2-picoline N-oxide anion. Recrystallization from ethyl acetate gives light tan crystals (47.2g, 33%), m.p. 98°–100° C.

Anal. Calcd, for $C_{15}H_{15}NO_3$: C, 70.02; H, 5.88; N, 5.44. Found: C, 69.98; H, 5.94; N, 5.35.

EXAMPLE 11

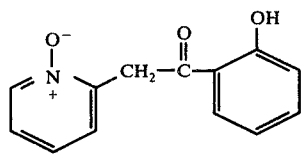

1-(2-Hydroxyphenyl)-2-(2-pyridinyl)ethanone N-oxide

A solution of 1-[2-(phenylmethoxy)phenyl]-2-(2-pyridinyl)ethanone N-oxide (50g) in acetic acid (125ml) is hydrogenated over 10% palladium on carbon catalyst (5g). The catalyst is filtered off and the filtrate is evaporated to give a black-green oil which crystallizes on standing. Recrystallization from ethyl acetate gives white crystals (28g, 78%), m.p. 154°–55° C.

Anal. Calcd. for $C_{13}H_{11}NO_3$: C, 68.11; H, 4.84; N, 6.11. Found: C, 68.19; H, 4.88; N, 6.15.

EXAMPLE 12

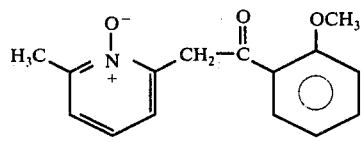

1-(2-Methoxyphenyl)-2-(6-methyl-2-pyridinyl)ethanone N-oxide 2,6-Lutidiene N-oxide (34.2g 0.3m) is added to sodium amide (11.5g, 0.3m) in anhydrous liquid ammonia. The resulting brown-orange anion is stirred one hour and then (25g, 0.15m) ethyl 2-methoxybenzoate is added dropwise. This reaction mixture is stirred for one hour and then quenched with ammonium chloride (33g). The ammonia is allowed to evaporate. The residue is dissolved in water and the resulting aqueous solution is extracted with chloroform. The extracts are washed with water, dried over $Na_2SO_4$, and evaporated under reduced pressure to give a red brown oil (15g).

EXAMPLE 13

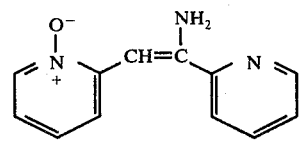

α-(2-pyridinyl)-2-pyridineethenamine 1-oxide

2-Picoline N-oxide (36.8g, 0.34m) is added to sodium amide (14g, 0.34m) in anhydrous liquid ammonia (300ml). The resulting anion is stirred for one hour and then ethyl picolinate (25g, 0.17m) is added dropwise.

The reaction is worked up as described in Example 1. Recrystallization gives dirty yellow crystals (13.2g, 37.2%), m.p. 156°–58° C.

Anal. Calcd. for $C_{12}H_{11}N_3O$: C, 67.59; H, 5.20; N, 19.71. Found: C, 67.33; H, 5.21; N, 19.48.

EXAMPLE 14

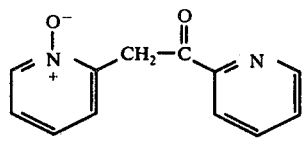

1,2(N-oxide)-di(2-pyridinyl)ethanone

Prepared by boiling α-(2-pyridinyl)-2-pyridineethenamine 1-oxide from Example 13 in water for two hours. Extraction of the aqueous solution with chloroform, drying over $Na_2SO_4$, and evaporation under reduced pressure gives a brown powder. Recrystallization from etyl acetate gives light brown crystals (2.85g, 95%), m.p. 139°–41° C.

Anal. Calcd. for $C_{12}H_{10}N_2O_2$: C, 67.28; H, 4.71; N, 13.08. Found: C, 67.12; H, 4.80; N, 12.99.

EXAMPLE 15

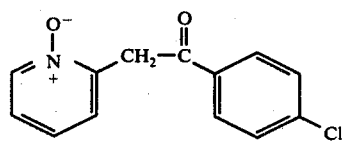

1-(4-Chlorophenyl)-2-(2-pyridinyl)ethanone N-oxide

Prepared by the general method described for Example 1 from methyl p-chlorobenzoate and 2-picoline N-oxide anion. Recrystallization from ethyl acetate gives light beige crystals (26.4g, 45.8%), m.p. 145°–48° C.

Anal. Calcd. for $C_{13}H_{10}ClNO_2$: C, 63.04; H, 4.07; N, 5.66; Cl, 14.31. Found: C, 63.09; H, 4.12; N, 5.56; Cl, 14.46.

EXAMPLE 16

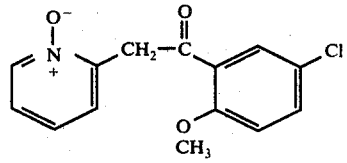

1-[5-Chloro-2-methoxyphenyl]-2-(2-pyridinyl)ethanone N-oxide

Prepared by the general method described for Example 1 from methyl 5-chloro-2-methoxybenzoate and 2-picoline N-oxide anion. Recrystallization from ethyl acetate gives light beige crystals (37.4g, 67.5%), m.p. 119°–23° C.

Anal. Calcd. for $C_{14}H_{12}ClNO_3$: C, 60.55; H, 4.36; N, 5.04; Cl, 12.77. Found: C, 60.34; H, 4.42; N, 4.90; Cl, 12.75.

EXAMPLE 17

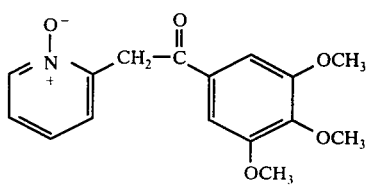

1-(3,4,5-Trimethoxyphenyl)-2-(2-pyridinyl)ethanone N-oxide

Prepared by the general method described for Example 1 from methyl 3,4,5-trimethoxybenzoate and 2-picoline N-oxide anion. Recrystallization from ethyl acetate gives white crystals (29.8g, 55.6%), m.p. 145°–48° C.

Anal. Calcd. for $C_{16}H_{17}NO_5$: C, 63,36; H, 5.65; N, 4.62. Found: C, 63.08; H, 5.65; N, 4.82.

EXAMPLE 18

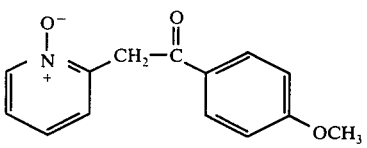

1-(4-Methoxyphenyl)-2-(2-pyridinyl)ethanone N-oxide

Prepared by the general method described for Example 1 from methyl p-methoxybenzoate and 2-picoline N-oxide anion. Recrystallization from ethanol gives beige crystals (34.3g, 59%), m.p. 132°–35° C.

Anal. Calcd. for $C_{14}H_{13}NO_3$: C, 69.12; H, 5.39; N, 5.76. Found: C, 68.87; H, 5.44; N, 5.68.

EXAMPLE 19

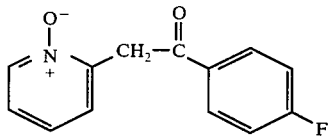

1-(4-Fluorophenyl)-2-(2-pyridinyl)ethanone N-oxide

Prepared by the general method described for Example 1 from ethyl p-flurobenzoate and 2-picoline N-oxide anion Recrystallization from ethyl acetate gives off-white crystals (27.9g, 50.8%), m.p. 111°–13° C.

Anal. Calcd. for $C_{13}H_{10}FNO_2$: C, 67.53; H, 4.36; N, 6.06; F, 8.22. Found: C, 67.33; H, 4.37; N, 5.97; F, 8.14.

EXAMPLE 20

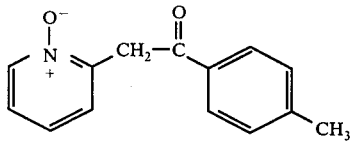

1-(4-Methylphenyl)-2-(2-pyridinyl)ethanone N-oxide

Prepared by the general method described for Example 1 from methyl p-methylbenzoate and 2-picoline N-oxide anion. Recrystallization from ethyl acetate gives tan crystals (15.2g, 25%), m.p. 148°–51° C.

Anal. Calcd. for $C_{14}H_{13}NO_2$: C, 73.99; H, 5.77; N, 6.16. Found: C, 73,80; H, 5.78; N, 6.09.

EXAMPLE 21

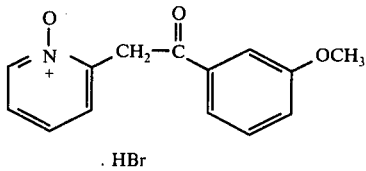

1-(3-Methoxyphenyl)-2-(2-pyridinyl)ethanone N-oxide hydrobromide

The ethanone N-oxide is prepared by the general method described for Example 1 from methyl 3-methoxybenzoate and 2-picoline N-oxide anion and isolated as a red brown oil. It is converted to the hydrobromide salt in a 50:50 mixture of refluxing acetic and hydrobromic acids. Removal of the acids under reduced pressure gives a solid product. Recrystallization from absolute ethanol gives white crystals (23.5g), m.p. 135°–40° C.

Anal. Calcd. for $C_{14}H_{14}BrNO_3$: C, 51,87; H, 4.35; N, 4.32; Br$^-$, 24.65. Found: C, 51.68; H, 4.40; N, 4.26; Br$^-$, 24.73.

We claim:

1. A process for preparing a compound of the formula IX:

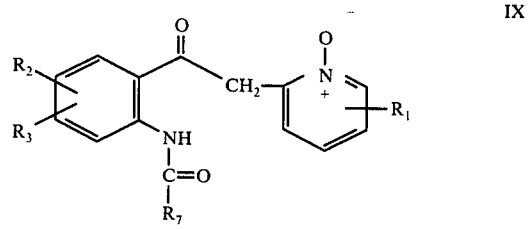

wherein $R_1$ is hydrogen or lower alkyl; $R_2$ and $R_3$ are each hydrogen, halogen, hydroxy, lower alkyl, lower alkoxy or benzyloxy; and $R_7$ is lower alkyl or phenyl; which comprises reacting a compound of the formula X:

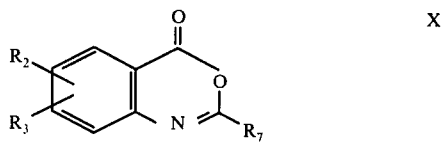

wherein $R_2$, $R_3$ and $R_7$ are as defined above in IX, with a substituted 2-picoline N-oxide of the formula V:

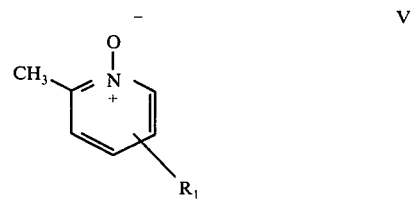

wherein $R_1$ is as defined above in IX in liquid ammonia in the presence of an alkali metal amide, to obtain a compound having the formula IX above.

* * * * *